United States Patent [19]

Mortreux et al.

[11] Patent Number: 5,128,488
[45] Date of Patent: Jul. 7, 1992

[54] PROCESS FOR THE ASYMMETRIC HYDROGENATION OF CARBONYL COMPOUNDS OBTAINED

[75] Inventors: André Mortreux, Hem; Françis Petit, Villeneuve D'Asco, both of France

[73] Assignee: Societe Chimique Des Charbonnages S.A., Paris, France

[21] Appl. No.: 515,314

[22] PCT Filed: Jun. 22, 1987

[86] PCT No.: PCT/FR87/00238
§ 371 Date: Apr. 1, 1988
§ 102(e) Date: Apr. 1, 1988

[87] PCT Pub. No.: WO87/07889
PCT Pub. Date: Dec. 30, 1987

Related U.S. Application Data

[63] Continuation of Ser. No. 165,111, Apr. 1, 1988, abandoned.

[30] Foreign Application Priority Data

Jun. 23, 1987 [FR] France .................... 86 09024

[51] Int. Cl.⁵ .................. C07D 307/60; C07C 235/36
[52] U.S. Cl. .................... 549/319; 564/170; 568/700; 568/880; 568/814; 568/388
[58] Field of Search ............... 564/170; 549/319; 568/700, 880, 814, 388

[56] References Cited

U.S. PATENT DOCUMENTS 3,968,147  7/1976  Solodar .................. 564/302 X
4,539,411  9/1985  Broger et al. ............ 548/402
4,556,740 12/1985  Hansen et al. ............ 564/302 X

FOREIGN PATENT DOCUMENTS 0136210  4/1985  European Pat. Off. .

OTHER PUBLICATIONS

M. Petit et al., Nouveau Journal De Chemie, vol. 7, No. 10, pp. 593-96, 1983.
H. B. Kagan, "Asymmetric Synthesis Using Organometallic Catalysts," Comprehensive Organometallic Chemistry, G. Wilinson, Ed. (1982) vol. 8, Pergamon Press, London, pp. 463-498.
K. Tani, "Preparation of New Chiral Peralkyldiphosphines as Efficient Ligands for Catalytic Asymmetric Hydrogenation of α-Dicarbonyl Compounds", J. Chem. Soc., Chem. Commun., 1984, pp. 1641-1643.

Primary Examiner—Allen J. Robinson
Assistant Examiner—Melvin Russell
Attorney, Agent, or Firm—Finnegan, Henderson, Farabow, Garrett & Dunner

[57] ABSTRACT

The asymmetric hydrogenation of carbonyl compounds is carried out in the presence of at least one transition metal complex MZq(M=metal of group VIII of the Periodic Classication; Z=ligand selected among the atoms and the molecules which may complex the metal M; and q=degree of corrdination of M) and of at least one chiral phosphorous-containing ligand having formula (I), wherein R is hydrocarbonated radical (alkyl, cycloalkyl and aryl); $R^1$ is H, hydrocarbonated radical or $PR_2$; $R^2$ is H or hydrocarbonated radical $R^3, R^4$, necessarily different, are H and optionally functionalized hydrocarbonated radicals; $R^5$ and $R^6$ are H and optionally functionalized hydrocarbonated radicals; one of the radicals $R^3$ and $R^4$ possibly carrying a function - $OPR_2$ or $NPR_2$, $R^5$ and $R^6$ being in this case H when $R^1$ is $PR_2$; $R^2$ and $R^3$ and the atoms of N and C which cary them respectively forming a heterocycle; or $R^2$ and $R^5$, the atoms of N and C which carry them respectively and the intermediate C atom possibly forming a heterocycle.

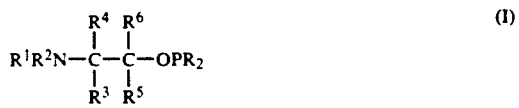

23 Claims, No Drawings

PROCESS FOR THE ASYMMETRIC HYDROGENATION OF CARBONYL COMPOUNDS OBTAINED

This application is a continuation of application Ser. No. 07/165,111 filed Apr. 1, 1988, now abandoned.

The present invention relates to the enantioselective synthesis of organic compounds and it relates more particularly to the asymmetric hydrogenation of carbonyl groups, catalyzed by transition metal complexes containing chiral phosphorus-containing ligands.

Although a reduction catalysed in a homogeneous phase by Wilkinson type complexes, $Rh[PPh_3]_3Cl$, prove to be very effective with respect to the asymmetric synthesis of α-amino acids from olefinic precursors (H. B. Kagan, "Asymmetric synthesis using organometallic catalysts, Comprehensive organometallic chemistry, G. Wilkinson Ed. (1982) Vol. 8, 463, Pergamon Press, London), it is inoperative, however, in the synthesis of chiral alcohols from ketones.

Moreover, in asymmetric catalysis, it is well known that the different types of ligands are specific for a given starting compound (substrate).

It has now been discovered that asymmetric hydrogenation of carbonyl compounds could be envisaged with excellent results by the use of ligands obtained in a single stage starting with chiral α-amino alcohols which are commercially produced or which are derived from natural α-amino acids, such ligands having already been described in European Patent Application EP-A-136,210 for other syntheses (such as asymmetric hydrogenation of dehydroamino acids) and by M. Petit, A. Mortreux, F. Petit, G. Buono and G. Peiffer in "Nouv. J. chim. 10 (7) (1983) 593".

Moreover, it has surprisingly been discovered that the choice of a reaction medium in which the substrate is soluble whereas the final product is insoluble enables, on the one hand, high optical yields to be achieved and, on the other hand, very high substrate:metal catalyst molar ratios (which may range up to 5000) to be employed, which has never been possible to achieve until now. Thus, these ratios are 50 and 200 in the case of the asymmetric hydrogenations of the carbonyl group, described by K. Yamamoto et al. and by K. Tani et al. respectively, the value 200 representing the upper limit which could be achieved so far.

The subject of the present invention is a process for the asymmetric hydrogenation of carbonyl compounds, which is carried out in the presence, on the one hand, of at least one transition metal complex of formula:

$$MZ_q$$

in which
M is a group VIII metal of the Periodic Table;
Z represents one or more among the atoms and molecules capable of complexing the metal M; and
q is the coordination number of the metal M,
and, on the other hand, of at least one chiral phosphoruscontaining ligand, wherein a compound represented by formula (I) is chosen as the chiral phosphorus-containing ligand:

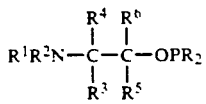

in which formula:
R represents a hydrocarbon radical chosen from amongst straight-chain or branched alkyl, cycloalkyl or aryl radicals;
$R^1$ represents a hydrogen, a hydrocarbon radical or a $-PR_2$ residue;
$R^2$ represents a hydrogen or a hydrocarbon radical;
$R^3$ and $R^4$, which are necessarily different, are chosen from amongst hydrogen atoms and hydrocarbon radicals optionally carrying at least one group chosen from amongst alcohol, thiol, thioether, amine, imine, acid, ester, amide and ether groups; and
$R^5$ and $R^6$ are chosen from amongst hydrogen atoms and optionally functionalized hydrocarbon radicals;
it being possible for one of the radicals $R^3$ and $R^4$ to carry an $-OPR_2$ or $-NPR_2$ group, both $R^5$ and $R^6$ being, in this case, equal to hydrogen when $R^1$ represents $-PR_2$,
it being possible for $R^2$ and $R^3$ and the nitrogen and carbon atoms which carry them respectively to together form a heterocycle;
or alternatively, it being possible for $R^2$ and $R^5$, the nitrogen and carbon atoms which carry them respectively and the intermediate carbon atoms to together form a heterocycle.

This family of ligands may be divided into three subfamilies depending on the number of dihydrocarbylphosphine ($-PR_2$) radicals present, i.e. monodentate chelates (in which $R^1$ does not refer to $-PR_2$ and $R^3$ does not carry the residue $-OPR_2$ or $-NPR_2$); bidentate chelates (in which either $R^1$ represents $-PR_2$ in which case $R^3$ and $R^4$ do not carry a $-OPR_2$ or $-NPR_2$ group, or $R^3$ or $R^4$ carry an $-OPR_2$ or $-NPR_2$ residue in which case $R^1$ cannot represent $-PR_2$) and tridentate chelates (in which $R^1$ represents a $-PR_2$ residue and $R^3$ carries an $-OPR_2$ or $-NPR_2$ residue).

As alkyl radicals for R, there will be mentioned $C_1-C_{12}$, especially $C_1-C_6$, alkyl radicals, for example methyl, ethyl, isopropyl and tert-butyl radicals. As cycloalkyl radicals for R, there will be mentioned cyclopentyl and cyclohexyl radicals. As aryl radicals for R, there will be mentioned the phenyl radical. Alkyl and cycloalkyl radicals are preferred for R.

As hydrocarbon radical for $R^1$ or $R^2$, there could be mentioned alkyl radicals, especially $C_1-C_{12}$ alkyl radicals, for example the methyl radical.

Examples of hydrocarbon radicals for $R^3$ or $R^4$ are, in particular, methyl, isopropyl, neobutyl, isobutyl, isoamyl, hydroxymethyl, n-hydroxyethyl, iso-hydroxyethyl, n-aminobutyl, 4-methyleneimidazolyl, N-n-propylguanidyl, ethanoyl, acetamido, n-propionyl, n-propionamido, phenyl, benzyl, para-hydroxybenzyl, 3-methyleneindolyl, mercaptomethyl, methylthioethyl and $NH_2-C(=NH)-NH-(CH_2)_3-$ radicals.

As hydrocarbon radicals for $R^5$ or $R^6$, there will be mentioned, in particular, $C_1-C_{12}$ alkyl radicals.

When the ligands of formula (I) contain a heterocycle, formed with the radicals $R^2$ and $R^3$ or $R^2$ and $R^5$, this heterocycle is especially a 5- or 6-membered heterocycle.

The process for the production of these ligands of formula (I) is described in European Patent Application EP-A-136,210. With regard to the complex $MZ_q$, as metals M which can be commonly employed, there may be mentioned iron, nickel, cobalt, rhodium, ruthenium, iridium, palladium and platinum; as atoms or molecules Z which can be commonly employed, there may be mentioned carbon monoxide, halogens, ethylene, norbornadiene, cyclooctadiene and acetylacetone. The coordination number q may commonly be between 2 and 6 inclusive depending on the metal M and/or the ligand Z employed.

Where appropriate, the hydrogenation reaction according to the invention may be carried out in the presence of at least one agent capable of taking up a ligand Z from the constituent $MZ_q$, it being possible for this agent to be either an acid containing an anion $A^-$ which has a low complexing capacity and which is sterically hindered or a metal salt of such an acid, or a quantity of electricity applied by electrolysis at an applied cathode potential. Anion $A^-$ which has a low complexing capacity and which is sterically hindered especially means the anions perchlorate, tetrafluoroborate, tetraphenylborate and hexafluorophosphate. The metal salts which can be employed are mainly those of silver and thallium.

This enantioselective synthesis reaction may be carried out in the presence of at least one activator chosen from amongst aluminum-containing derivatives of formula $AlR'_n X_{3-n}$ in which n has a value from 0 to 3, X is a halogen atom and R' an alkyl radical containing from 1 to 12 carbon atoms.

The complex $MZ_q$ and the ligand of formula (I) are generally in a molar ratio ligand:complex of between 1 and 10. The complex $MZ_q$ and the aluminum-containing derivative mentioned above are in a molar ratio aluminum-containing derivative:complex of between 0.1 and 10. The complex $MZ_q$ and the agent capable of taking up at least one ligand Z are generally in a molar ratio agent: complex less than or equal to q, when this agent is an acid or a salt.

The hydrogenation reaction is generally carried out at a temperature of between $-20°$ C. and $200°$ C. for a period of between approximately 5 minutes and 24 hours and at a pressure of between 1 and 200 bars.

Moreover, the molar ratio of the substrate (starting compound) to the catalyst metal M may reach high values of 5000, even 10,000 or above. In order to be able to work at these high values, the following specific embodiment is employed:

The hydrogenation is carried out in a (solvent or solvent mixture) medium in which the substrate is substantially soluble, but in which the reaction product is insoluble or substantially insoluble and therefore precipitates as it is being formed.

In order to obtain a better enantiomeric excess, there may be mentioned, as solvents, aromatic hydrocarbon solvents such as benzene, toluene and xylene, aliphatic alcohols such as ethanol and aliphatic or alicyclic ethers, especially ethyl ether, dioxane and tetrahydrofuran, and compatible mixtures of these solvents.

Among starting carbonyl compounds employed in this hydrogenation reaction, there may be mentioned α-keto amides such as N-benzylbenzoylformamide ($PhCOCONHCN_2Ph$) or N-benzyl-4-hydroxybenzoylformamide, which are readily synthesized by the dicarbonylation of aryl halides catalyzed by palladium complexes: α-dicarbonyl compounds such as 2-oxo-3,3-dimethyl-1,4-butanolide (pentoyllactone) and α-keto esters.

In order to make the subject of the present invention better understood, several examples of implementation thereof will now be described.

In Table I below, the nomenclature of the ligands employed is given.

TABLE 1

| Nomenclature of Ligands employed | | |
|---|---|---|
| (structure with $CH_2OPCy_2$, $CH_3-C-H$, $NPCy_2$, $CH_3$) | CyAlaNOP | (S)—1-0-dicyclohexylphosphino)-2-N—methyl-N—dicyclohexylphosphinopropane |
| (structure with $CH_2OPCy_2$, $CH_3$, H, $NPCy_2$, $OPCy_2$, $CH_3$) | CyThreoNOP | (2R,3R)—1,3-bis-O—dicyclohexylphosphino-2-N—methyl—N—dicyclohexylphosphinobutane |
| (pyrrolidine structure with H, $CH_2OP(i-Pr)_2$, $P(i-Pr)_2$) | i-PrProNOP | (S)-N-diisopropylphosphino-2-diisopropylphosphinoxymethyl-pyrrolidine |
| (pyrrolidine structure with H, $CH_2OPCy_2$, $PCy_2$) | CyProNOP | (S)-N-dicyclohexylphosphino-2-dicyclohexylphosphinoxymethyl-pyrrolidine |
| (pyrrolidine structure with H, $CH_2OPCy_2$, H) | CyProNHOP | (S)-2-dicyclohexylphosphinoxymethyl-pyrrolidine |

TABLE 1-continued

| Nomenclature of Ligands employed | | |
|---|---|---|
| [structure: pyrrolidine with CH₂OPPh₂ and PPh₂] | ProNOP | (S)-N-diphenylphosphino-2-diphenylphosphinoxy-methyl-pyrrolidine |
| [structure: pyrrolidine with PPh₂O, CONHBu, PPh₂] | Pro-BuNOP | (2S,4R)-N-diphenylphosphino-4-diphenylphosphino-2-n-butyl-formamide |

I—PREPARATION OF THE LIGANDS a) Preparation of the Ligand CyProNOP 2.53 g (0.025 mol) of prolinol and 14 cm³ (0.1 mol) of $NEt_3$ dissolved in 50 cm³ of anhydrous benzene, are introduced into a 250 cm³ round-bottomed flask. 11.64 g of $PCy_2Cl$ dissolved in 50 cm³ of the same solvent are added dropwise at 0° C. The reaction mixture is then maintained stirred for 12 hours. The solution is then filtered in order to remove the triethylamine hydrochloride therefrom and the solvent removed under vacuum. The ligand is purified by chromatography on silica gel (eluent: ethyl acetate:$NEt_2H$ in a ratio of 98:2 by volume).

b) The other ligands are prepared according to the same procedure.

II—CATALYTIC HYDROGENATION OF VARIOUS CARBONYL COMPOUNDS ACCORDING TO THE PRESENT INVENTION a) General Procedure $6.6 \times 10^{-5}$ mmol of ligand is dissolved in 15 cm³ of anhydrous benzene in a tube under nitrogen.

14.8 mg ($3 \times 10^{-5}$ mol) of the complex [Rh(cyclooctadiene)Cl]₂ are weighed into another tube and the ligand solution is added thereto by a transfer tube. The whole mixture is maintained stirred for 15 minutes.

$1.2 \times 10^{-2}$ mole of the starting compound dissolved in 15 cm³ of benzene is introduced, under a hydrogen atmosphere, into a thermostated (25° C.) glass reactor after purging it several times (hydrogen-vacuum). The catalytic solution is then transferred into the reactor and the progress of the reaction is monitored by noting the volume of hydrogen consumed.

The final product is then isolated from the reaction medium.

b) Preparation of the Final Product

1—Preparation of (S)-N-benzylmandelamide starting with N-benzylbenzoylformamide

When the reaction is complete, the solution in benzene is filtered and the precipitate formed by the reaction is washed with $2 \times 10$ cm³ of cold benzene. The yield is of the order of 95–100%.

The specific rotation $a_D^{25}$ is determined on a solution in trichloromethane at a concentration of 1.09 g/100 cm³. The enantiomeric excess is calculated from the $a_D^{25}$ for the pure product, which is +79.9° C. (see Table II).

2—Preparation of 2-hydroxy-3,3-dimethyl-1,4-butanolide starting with 2-oxo-3,3-dimethyl-1,4-butanolide (pentoyllactone)

When the reaction is complete, the solvent is evaporated off and the residue distilled under vacuum. The yield is of the order of 90–100%.

The specific rotation $a_D^{25}$ is determined on an aqueous solution at a concentration of 2.05 g/100 cm³. The enantiomeric excess is calculated from the $a_D^{25}$ for the pure product, which is −50.7°.

A number of examples of asymmetric hydrogenation according to the invention, performed according to the general procedure described in paragraph IIa), are summarized in Tables II to IV below, Table IV illustrating the importance of the choice of solvent (the product of reduction of the substrate n-benzylbenzoylformamide is soluble in ethanol and not in benzene).

TABLE II

| | Asymmetric hydrogenation of carbonyl compounds in the presence of [RH-L]entities (L = ligand). | | | | | |
|---|---|---|---|---|---|---|
| Starting compound or substrate (S) | Ligand (L) | Solvent | Reaction period | Yield (%) | Enantiomeric excess (%) | Configuration |
| PhCOCNHCH₂Ph | CyProNOP | Benzene | 6 hours | 95 | 85.6 | S |
| " | " | " | " | 90 | 85.5[a] | S |
| " | " | " | " | 98 | 83[b] | S |
| " | " | " | " | 98 | 86[c] | S |
| " | i-PrProNOP | " | " | 97 | 77 | S |
| PhCONHCH₂Ph | CyProNOP | Benzene:ethanol | " | 100 | 66 | $a_D^{20} = +34.5$ C = 1, ethanol) |

(2:1)

TABLE II-continued

Asymmetric hydrogenation of carbonyl compounds in the presence of [RH-L]entities (L = ligand).

| Starting compound or substrate (S) | Ligand (L) | Solvent | Reaction period | Yield (%) | Enantiomeric excess (%) | Configuration |
|---|---|---|---|---|---|---|
| 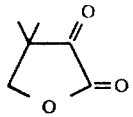 | CyProNOP | Benzene | 5 hours | 90 | 49.2 | R |
| " | " | " | 6 hours | 100 | 49.2 | R |
| " | i-PrProNOP | " | 5 hours | 100 | 49.5 | R |
| " | CyProNOP | Tetrahydrofuran | 5 hours | 100 | 46 | R |

General Experimental Conditions $[S]:[Rh]=200$; $[S]=0.4M$; $[Rh]=2\times10^{-3}M$
$[L]=2.2\times10^{-3}M$
Quantity of solvent = 30 cm$^3$
Temperature = 25° C.
$H_2$ pressure = 1 bar

Specific Experimental Conditions (a): $[S]:[RH]=400$; $[RH]=10^{-3}M$
(b): $[S]:[Rh]=1000$; $[Rh]=4\times10^{-4}M$
(c): $[S]:[Rh]=5000$; $[Rh]=8\times10^{-5}M$

TABLE III

Hydrogenation of the substrate N-benzylbenzoylformamide PhCOCONHCH$_2$Ph

| Ligand L | L:Rh ratio | Hydrogenation rate (cm$^3$ of hydrogen consumed per minute) | Half-reaction time (min) | Enantriomeric excess (%) | Configuration |
|---|---|---|---|---|---|
| CyProNOP | 1.1 | 2.3 | 43 | 86.6 | S |
| CyProNHOP | 1.1 | 0.6 | 200 | 48.7 | S |
| CyProNHOP | 2.2 | 0.65 | 200 | 49.7 | S |
| CyThreoNOP | 1.1 | 1.8 | 67 | 81.5 | S |
| CyAlaNOP | 1.1 | 2 | 55 | 74.4 | S |
| i-PrProNOP | 1.1 | 1.5 | 70 | 77 | S |
| ProNOP[a] | 1.1 | — | — | 46 | S |
| Pro-BuNOP[a] | 1.1 | — | — | 49.3 | S |

Experimental Conditions $[Rh]=2\times10^{-3}M$; $[S]:[Rh]=200$
Solvent: benzene (30 cm$^3$)
Temperature: 25° C.
Pressure: approximately 1 bar
Yield: greater than 90%
(a): Different reaction conditions, which are: pressure 40 bars; temperature 30° C. and reaction time 12 h.

TABLE IV

Effect of the molar ratio [S]:[Rh] during the reduction of N-benzylbenzoylformamide PhCOCONHCH$_2$ with the system "Rh.CyProNOP. Cl"

| Substrate (S) | Solvent | Half-reaction time (min) | Yield (%) | Enantiomeric excess (%) | Configuration |
|---|---|---|---|---|---|
| 200 | Benzene | 55 | 95 | 85.6 | (S) |
| 400 | Benzene | 60 | 90 | 85.5 | (S) |
| 1000 | Benzene | 62 | 98 | 83 | (S) |
| 5000 | Benzene | 60 | 91 | 86 | (S) |
| 200 | Ethanol | 170 | 88 | 72 | (S) |
| 400 | Ethanol | 185 | 92 | 43.7 | (S) |

Experimental Conditions $[S]=0.4M$
$[L]:[Rh]=1.1$
Solvent: benzene (30 cm$^3$)
Temperature: 25° C.
Pressure: approximately 1 bar

We claim:

1. A process for the asymmetric hydrogenation of the carbonyl moiety of a carbonyl compound comprising the step of contacting a carbonyl moiety of a carbonyl compound with hydrogen in the presence of at least one transition metal complex of the formula:

MZq in which
M is a group VIII metal of the Periodic Table;
Z is at least one ligand selected from the group consisting of atoms and molecules capable of complexing the metal M; and
q is the coordination number of the metal M,
and at least one chiral phosphorus-containing ligand of the formula (I):

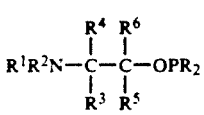

in which:
R is a hydrocarbon radical selected from the group consisting of straight-chain or branched alkyl, cycloalkyl and aryl radicals;

$R^1$ is a hydrogen, a hydrocarbon radical or a —$PR_2$ residue;

$R^2$ is a hydrogen or a hydrocarbon radical;

$R^3$ and $R^4$, which are necessarily different, are selected from the group consisting of hydrogen atoms, hydrocarbon radicals and hydrocarbon radicals carrying at least one group selected from the group consisting of alcohol, thiol, thioether, amine, imine, acid, ester, amide and ether groups; and $R^5$ and $R^6$ are selected from the group consisting of hydrogen atoms, hydrocarbon radicals and functionalized hydrocarbon radicals; it being possible for one of the radicals $R^3$ and $R^4$ to carry an —$OPR_2$ or —$NPR_2$ group, both $R^5$ and $R^6$ being, in this case, equal to hydrogen when $R^1$ represents —$PR_2$, it being possible for $R^2$ and $R^3$ and the nitrogen and carbon atoms which carry them respectively to together form a 5- or 6-membered heterocycle, or alternatively, it being possible for $R^2$ and $R^5$, the nitrogen and carbon atoms which carry them respectively and the intermediate carbon atoms to together form a 5- or 6-membered heterocycle, to thereby asymmetrically hydrogenate said carbonyl moiety of said carbonyl compound.

2. The process as claimed in claim 1, wherein for R the straight chain or branched alkyl radical is a $C_1$-$C_{12}$ alkyl radical.

3. The process as claimed in claim 1, wherein for R the cycloalkyl radical is a cyclohexyl or cyclopentyl radical.

4. The process as claimed in claim 1, wherein for R the aryl radical is a phenyl radical.

5. The process as claimed in claim 1, wherein for $R^1$ and $R^2$ the hydrocarbon radical is a $C_1$-$C_{12}$ alkyl radical.

6. The process as claimed in claim 1, wherein for $R^3$ and $R^4$ the hydrocarbon radical is a methyl, isopropyl, isobutyl, isoamyl, neobutyl, hydroxymethyl, n-hydroxyethyl, iso-hydroxyethyl, n-aminobutyl, 4-methyleneimidazolyl, N-n-propylguanidyl, ethanoyl, acetamido, n-propionyl, n-propionamido, phenyl, benzyl, para-hydroxybenzyl, 3-methyleneindolyl, methanethioyl, mercaptomethyl or $NH_2$—C(=NH)—$NH(CH_2)_3$— group.

7. The process as claimed in claim 1, wherein for $R^5$ and $R^6$ the hydrocarbon radical is a $C_1$-$C_{12}$ alkyl radical.

8. The process as claimed in claim 1, wherein the metal M of the complex MZq is iron, nickel, cobalt, rhodium, ruthenium, iridium, palladium or platinum.

9. The process as claimed in claim 1, wherein the atom or molecule Z of the complex MZq is carbon monoxide, halogens, ethylene, norbornadiene, cyclooctadiene or acetylacetone.

10. The process as claimed in claim 1, wherein q of the complex MZq is a value between 2 and 6 inclusive.

11. The process as claimed in claim 1, wherein the hydrogenation is carried out in the presence of at least one agent capable of taking up a ligand Z from the constituent MZq, it being possible for this agent to be either an acid having an anion $A^-$ which has a low complexing capacity and which is sterically hindered or a metal salt of such an acid, *or* a quantity of electricity applied by electrolysis at an applied cathode potential.

12. The process as claimed in claim 1, wherein the hydrogenation is carried out in the presence of at least one activator selected from aluminum-containing derivatives of formula $AlR'_nX_{3-n}$, in which n has a value from 0 to 3, X is a halogen atom and R' is an alkyl radical containing from 1 to 12 carbon atoms.

13. The process as claimed in claim 1, wherein the reaction is carried out using a molar ratio ligand of formula (I): complex MZq of between 1 and 10.

14. The process as claimed in claim 11, wherein the reaction is carried out using a molar ratio agent capable of capturing a ligand Z:complex MZq less than or equal to q.

15. The process as claimed in claim 12, wherein the reaction is carried out using a molar ratio activator:complex MZq of between 0.1 and 10.

16. The process as claimed in claim 1, wherein the reaction is carried out at a temperature of between −20° C. and 200° C. and at a pressure of between 1 and 200 bars.

17. The process as claimed in claim 1, wherein the reaction is carried out in a medium in which the carbonyl compound starting material is substantially soluble, but in which the reaction product is insoluble or substantially insoluble.

18. The process as claimed in claim 1, wherein the reaction is carried out in a solvent selected from the group consisting of aromatic hydrocarbon solvents, aliphatic alcohols, aliphatic and alicyclic ethers and their mixtures.

19. The process as claimed in claim 1, wherein hydrogenation is carried out with a substrate selected from the group consisting of α-keto amides and α-dicarbonyl compounds.

20. The process as claimed in claim 2, wherein the straight chain or branched alkyl radical is methyl, ethyl, isopropyl, or tert-butyl.

21. The process as claimed in claim 17, wherein the molar ratio of carbonyl compound starting material to catalyst is at least 5,000 to 1.

22. The process as claimed in claim 21, wherein the molar ratio of carbonyl compound starting material to catalyst is at least 10,000 to 1.

23. The process as claimed in claim 19, wherein the α-keto amides are selected from the group consisting of N-benzylbenzoyl-formamide and N-benzyl-4-hydroxybenzoylformamide and the α-dicarbonyl compounds are selected from the group consisting of 2-oxo-3,3-dimethyl-1,4-butanolide and α-keto esters.

* * * * *

UNITED STATES PATENT AND TRADEMARK OFFICE
CERTIFICATE OF CORRECTION

PATENT NO. : 5,128,488
DATED : July 7, 1992
INVENTOR(S) : Andre Mortreux et al.

It is certified that error appears in the above-identified patent and that said Letters Patent is hereby corrected as shown below:

```
Title Page, Title, after "COMPOUNDS" insert --AND COMPOUNDS--;
    Front Page, Inventors, change "Françis Petit" to --Francis
         Petit--;
    Front Page, Inventors, change "Villeneuve D'Asco" to
         --Villeneuve d'Ascq--; and
    Front Page, Priority Data, change "Jun. 23, 1987" to
         --Jun. 23, 1986--.

Abstract, line 4, change "Classication" to --Classification--;
    Abstract, line 6, change "corrdination" to --coordination--;
    Abstract, line 7, change "phosphorous-containing" to
         --phosphorus-containing--; and
    Abstract, line 17, change "cary" to --carry--.
```

Claim 5, column 9, line 34, change "$C_1-Cl_2$" to --$C_1-C_{12}$--.

Signed and Sealed this

Tenth Day of August, 1993

Attest:

MICHAEL K. KIRK

*Attesting Officer*    *Acting Commissioner of Patents and Trademarks*